United States Patent [19]

Ingvorsen et al.

[11] Patent Number: 5,116,744
[45] Date of Patent: May 26, 1992

[54] MICROBIAL CYANIDE CONVERTING ENZYMES, THEIR PRODUCTION AND USE

[75] Inventors: Kjeld Ingvorsen; Sven E. Godtfredsen; Birgitte Hojer-Pedersen, all of Vaerloese, Denmark

[73] Assignee: Novo Industri A/S, Bagsvaerd, Denmark

[21] Appl. No.: 595,684

[22] Filed: Sep. 19, 1990

Related U.S. Application Data

[63] Continuation of Ser. No. 167,720, Mar. 14, 1988, abandoned.

[30] Foreign Application Priority Data

Mar. 12, 1987 [DK] Denmark .............................. 1283/87

[51] Int. Cl.$^5$ ....................... C12P 13/00; C12N 9/78
[52] U.S. Cl. .................................. 435/128; 435/221; 435/232; 435/262; 435/829; 210/632; 210/606; 210/904
[58] Field of Search ............... 435/232, 227, 262, 824, 435/128; 210/632, 606, 904

[56] References Cited

U.S. PATENT DOCUMENTS

| | | | |
|---|---|---|---|
| 3,756,947 | 0/1973 | Fuji et al. ............................. | 210/11 |
| 3,940,332 | 0/1976 | Kato et al. ........................... | 195/2 |
| 4,440,644 | 4/1984 | Mudder et al. ..................... | 214/611 |
| 4,461,834 | 0/1984 | Mudder et al. ..................... | 435/253 |

FOREIGN PATENT DOCUMENTS 61249 9/1982 European Pat. Off. .
114423 8/1984 European Pat. Off. .

OTHER PUBLICATIONS

Fry, W. E., et al. (1975) Physiol. Plant Pathol. 7, 23-33.
Fry, W. E., et al. (1977) Phytopathology 67(7), 1001-1006.
Ingrorsen, K., et al. (1991) App. Environ. Microbiol. 57(6), 1783-1789.
Knowles, C. J., et al. (1986) Advances in Microbial Physiology 27, 73, 111.
Fry, W. E., et al. (1972) Arch. Biochem. Biophys 151, 468-474.
Anderson, P. M. (1980) Biochemistry 19, 2882-2888.
Chemical Abstract vol. 82 (11): 71608h—Mar. 17, 1975, p. 331.

Primary Examiner—Charles L. Patterson
Attorney, Agent, or Firm—Fidelman & Wolffe

[57] ABSTRACT

A novel cyanide converting enzyme, a "cyanidase" is described.

The enzyme is extremely efficient in reducing substantial concentrations of cyanide to very low levels in a broad pH, and temperature range, and in the presence of organics and metal ions.

20 Claims, No Drawings

MICROBIAL CYANIDE CONVERTING ENZYMES, THEIR PRODUCTION AND USE

This application is a continuation of United States application Ser. No. 07/167,720 filed Mar. 14, 1988.

TECHNICAL FIELD

The present invention relates to novel and improved bacterial cyanide converting enzymes which are active at high concentrations of inorganic cyanide under a wide range of environmental conditions, to their production and to their use in detoxification of cyanide containing streams.

BACKGROUND OF THE INVENTION

Discharge of industrial waste water containing inorganic cyanide into rivers, lakes and sea water causes serious environmental pollution. Hereinafter inorganic cyanide comprises cyanide ions and hydrogen cyanide.

Cyanide containing waste water is produced by a great variety of industrial manufacturing processes such as mining of precious metals, electroplating and production of synthetic fibres, polymers, food additives and food products.

Due to its high toxicity and abundant use in industrial processes, inorganic cyanide is among the highest ranking pollutants on EPA's List of Priority Pollutants (cf. *Environ.Sci.Technol.* 13 (1979), 416-422).

Some European countries have issued regulations demanding that waste water discharged into recipient waters must contain less than about 0.5 ppm of inorganic cyanide.

It is well established that about 2,000 species of higher plants are cyanogenic (i.e. contain organic cyanide compounds) and that these plants release significant amounts of inorganic cyanide upon decay or during post harvest processing. Cyanogenic plants include important agricultural crops such as cassava, sorghum, alfalfa, beans, peaches and almonds, some of which may contain high levels of cyanide (up to about 3 g of cyanide per kg of plant tissue).

In areas where the above-mentioned crops constitute the main diets, whole populations are likely to suffer from chronic cyanide poisoning (cf. page 101 and 122 in *Cyanide in Biology*, B. Vennesland, E. E. Conn, C. J. Knowles, J. Westley and F. Wissing, Eds., 1981, Academic Press, London and New York).

Degradation, conversion and detoxification of inorganic cyanide is, therefore, a matter of great importance in connection with 1) waste water treatment, 2) chemical manufacturing and 3) human nutrition.

Pure chemical processes for the conversion of the inorganic cyanide in cyanide containing waste streams have been practiced for many years. Conventional chemical treatment methods include alkaline chlorination, hydrogen peroxide treatment, ion exchange or electrolysis. These processes are expensive and in many instances impractical on a large scale. Furthermore, alkaline chlorination is a destructive process which may lead to the formation of chlorinated organic compounds which themselves are serious pollutants.

Several biological methods of treating cyanide containing waste waters have been proposed and practiced including acclimated sludge processes and various biological filter systems (cf. Howe, R.H.L., 1965, *Int.J.Air Water Poll.* 9, 463-478).

U.S. patent specifications Nos. 3,756,947, 3,940,332, 4,461,834 and 3,660,278 teaches the use of specially prepared sludge systems comprising 1) the seeding of activated sludge with cyanide converting microorganisms and 2) acclimation of the mixed system for one to several weeks prior to use. The sludge based systems described in these four U.S. patent specifications have, according to their claims, a very limited capacity of cyanide conversion—only waste water containing less than 50-250 ppm (2-10 mM) of cyanide ion can be efficiently decontaminated. Industrial waste water may contain considerably higher concentrations of cyanide.

Biotreatment systems using any kind of adjusted sludge with or without the addition of specific and viable cyanide converting microorganisms may be difficult to maintain and are not suitable for small scale operation. Also, sludge based systems are restricted to waste water treatment and obviously not practicable for, for example, cyanide conversion in food processing and for removal of cyanide residues in chemical product streams.

Enzymatic processes for the conversion of cyanide to formamide using fungal cells or immobilized fungal cells have been described in two European patent (publication Nos. 61,249 and 116,423). These patents claim the use of enzymes (enzyme: formamide hydro-lyase alias cyanide hydratase, EC 4.2.1.66) all of which were produced from fungi, mostly species of known phytopathogenic fungi. Cyanide was converted with 98% efficiency or down to about 1 ppm of inorganic cyanide at a temperature of 0-35° C. and a pH value of 6-10. Widespread technical use of cyanide converting enzymes produced from phytopathogenic fungi is however, problematic unless the commercial products are made completely sterile with respect to production strains.

There have been several reports (cf. Knowles and Bunch (*Adv.Micr.Physiol.* (1986), 73-111, Eds.: A. H. Rose and D. W. Tempest, Academic Press, London and New York) on the isolation of cyanide converting bacteria. Some of these bacterial strains are no longer available and according to the reports none of these bacteria produce enzymes which can convert high concentrations of inorganic cyanide to very low concentrations.

In none of these reports the enzymatic pathways of the cyanide conversions and the intermediates of the reactions have been identified clearly.

For example, bacterial isolates ATCC 39204 (U.S. patent specification No. 4,461,834); ATCC 21697 and ATCC 21698 (U.S. patent specification No. 3,756,947); ATCC 21930 (U.S. patent specification No. 3,940,332) and ATCC 21419 (U.S. patent specification No. 3,660,278) were claimed to have cyanide converting properties. Strains ATCC 21697 and ATCC 21698 stated in U.S. patent specification No. 3,756,947 to be *Achromobacter nitriloclastes* and *Alcaligenes viscolactis*, were reclassified as *Bacillus subtilis* and *Corynebacterium sp.*, respectively, upon deposition at ATCC (ATCC: American Type Culture Collection, 12301 Parklawn Drive, Rockville, Maryland, USA). Of the last-mentioned 5 strains thus quoted as producers of cyanide converting enzymes, only ATCC 21930 (*Corynebacterium sp.*) was actually found to exhibit such activity when tested thoroughly in our laboratory. The cyanide converting enzyme system of ATCC 21930 was, however, found to be inactivated rapidly at low cyanide concentrations (less than or equal to 20 mM).

At higher concentrations, the enzyme system was found to be completely inactive.

The scientific information available through patents cited hereinbefore and articles cited in the above recent review paper by Knowles and Bunch indicate that factors such as phytopathogenicity of production strains, enzyme inhibition and enzyme inactivation by cyanide are the primary obstacles to the technical use of enzymes for cyanide detoxification.

It has now surprisingly been found that certain gram-negative bacterial isolates belonging to the genus Alcaligenes produce cyanide converting enzymes with properties which are highly superior to the ones described to date. Such superior properties include e.g., tolerance towards high cyanide concentrations and substrate kinetic features which allow detoxification of cyanide to very low concentrations. Two bacterial isolates producing such superior cyanide converting enzymes have both been identified by DSM (Deutsche Sammlung von Mikroorganismen, Gottingen, Federal Republic of Germany) as species of *Alcaligenes denitrificans* subs. *denitrificans* and they have been deposited at DSM under the numbers DSM 4009 and DSM 4010 in connection with the present patent specification. The cyanide converting enzymes of DSM 4009 and DSM 4010 which catalyze the direct hydrolysis of inorganic cyanide to formic acid and ammonia are clearly different from other known cyanide converting enzymes such as: cyanide hydratase (formamide hydro-lyase E.C. 4.2.1.66), cyanide oxygenase, B-cyanoalanine synthase and others described in the paper by Knowles and Bunch (in Adv.Micr.Physiol. (1986), 73–111, cf. above).

The name Cyanidase is, therefore, proposed as a new name for this novel enzyme type produced by DSM 4009 and DSM 4010; an enzyme class which catalyzes the direct conversion of inorganic cyanide to formic acid and ammonia (i.e. without the intermediacy of formamide).

Cyanide converting enzymes (including cyanidase) have not previously been described in other Alcaligenes species and test in our laboratory has shown that they are not produced either constitutively nor inducibly by registered type strains of *Alcaligenes denitrificans* subs. *denitrificans* (DSM 30026 and NCIB 11961 (National Collection of Industrial Bacteria, Torry Research Station, Aberdeen, Scotland) nor by Alcaligenes species deposited as NCIB 10109, NCIB 8687, ATCC 31371 and DSM 30030.

It, therefore, seems appropriate to recognize the two isolates DSM 4009 and DSM 4010 of this invention either a new species of Alcaligenes or as new subtypes (variants) of *Alcaligenes denitrificans* characterized by their elaboration of a novel type of cyanide hydrolyzing enzyme—a so-called Cyanidase.

The enzymes of the present invention which are capable of converting inorganic cyanide are consequently hereinafter designated "cyanidases" or "cyanide converting enzymes".

SUMMARY OF THE INVENTION

Consequent to the findings of the inventors the invention in one aspect relates to novel bacterial origin cyanide converting enzyme systems, i.e., originating from microorganisms.

A further object of this invention is to furnish cyanide converting enzymes originating from microorganisms having no or minor patogenicity to plants and/or to animals.

A further object of this invention is to furnish cyanide converting enzymes having excellent stability at room temperature.

A further object of this invention is to furnish cyanide converting enzymes which are active in high concentrations of inorganic cyanide.

A further object of this invention is to furnish cyanide converting enzymes which are able to deplete inorganic cyanide to very low concentrations.

A further object of this invention is to furnish cyanide converting enzymes having high affinity towards inorganic cyanide.

A further object of this invention is to furnish cyanide converting enzymes which are active in the presence of organic solvents such as acetone and methanol, or other organic compounds such as nitriles.

A further object of this invention is to furnish cyanide converting enzymes having an improved activity in the presence of metal ions, e.g., of zinc, nickel, iron, silver, gold.

DETAILED DESCRIPTION OF THE INVENTION

As indicated above it has now, surprisingly, been found that certain bacteria, for example strains of *Alcaligenes denitrificans* subsp. denitrificans are able to produce cyanide converting enzymes having superior properties such as high tolerance and affinity towards inorganic cyanide and, furthermore, enzymes fulfilling most or all of the above objects can be prepared. The presence of such enzymes in bacteria has not been documented previously. Also enzymes with such properties are not produced by registered type of strains of *Alcaligenes denitrificans* subsp. denitrificans (e.g. DSM 30026 or NCIB 11961 (NCIB is the national Collection of Industrial Bacteria, Torry Research Station, Aberdeen, Scotland)) nor by Alcaligenes species deposited as NCIB 10109, NCIB 8687, ATCC 31371 and DSM 30030.

The novel, superior enzymes of this invention have been shown to be active at concentrations up to at least 26,000 ppm of inorganic cyanide which is to say 0.1M preferably 0.5M and to reduce cyanide concentration to less than 1ppm preferably 0.1ppm. The inorganic cyanide is converted to formic acid and ammonia by the enzymes.

The cyanide converting enzymes according to the present invention may be obtained from *Alcaligenes denitrificans* subsp. *denitrificans* and *alcaligenes sp.* of which two strains have been deposited at Deutsche Sammlung von Mikroorganismen, Gottingen, Federal Republic of Germany (hereinafter designated DSM), on Feb. 23, 1987 under the numbers DSM 4009 and DSM 4010, respectively for patent purposes under the conditions of the Budapest Treaty. These bacteria are mere examples of microorganisms which may be applied according to the present invention. Any microbial species capable of producing the cyanide converting enzymes of the herein described desirable properties can thus be used.

Cyanide converting enzymes can be produced by cultivating said microorganisms in liquid media in the presence of cyanide when inducible strains such as DSM 4009 and DSM 4010 are used. Cultivation in cyanide containing media will not be necessary when constitutive strains are discovered or mutants of DSM 4009, 4010 are employed, e.g., DF-34 ATCC 53754 a constitutive mutant of DSM 4009. Cultivation is carried out aerobically at a temperature of about 20-40° C., preferably about 30° C. and a pH value in the range of about 6 to 9.

The cyanidases of the invention may also be produced by inserting a gene coding for the expression of a cyanidase or a modified cyanidase into a suitable host, and cultivating said host microorganism.

The cyanide converting process is carried out at a pH value close to a pH-optima of the particular enzymes used. Typically this pH value would be around neutral i.e., pH 6-9. For treatment of waste streams exhibiting acid or basic pH values, cyanide converting enzymes having low or high pH-optima, respectively, can be used. The pH value can be in the range from about 4 to 11 preferably pH 6-9. During reaction, the temperature should be above the freezing point of the reaction mixture and preferably below about 60° C., for example in the range from about 15° to about 50° C., preferably 27°-45° C., and most preferred about 35° C.

The cyanide converting enzymes may be applied as intact cells, treated cells, a modified cell slurry, dried cells, a crude enzyme solution, a purified enzyme, all of which may be crosslinked, chemically modified or optionally bonded to or absorbed on a carrier. Cell mass preparations are a preferred enzyme form, e.g., cells cross-linked with glutaraldehyde.

The cyanidases produced by DSM 4009 and DSM 4010 have been found to be cellularly bound.

Some of the cyanidases of this invention are extremely stable. For example, washed cell slurries of DSM 4009 has been shown to retain more than about 95% of the initial enzyme activity when stored for a long period of time, for example more than 30 days at 22° C. At lower temperatures, enzyme stability is further increased.

The enzymes of this invention have high tolerance and affinity for inorganic cyanide, some being able to detoxify solutions containing at least 26,000 ppm of cyanide ion, i.e. about 1.0M. Also, the residual concentration of inorganic cyanide of solutions to which enzymes of this invention are added can be reduced to less than about 0.03 ppm. Additional valuable features of some enzymes of this invention are their ability to efficiently convert inorganic cyanide in the presence of organic solvents and nitriles (for example acetone, methanol methacrylonitrile and acrylonitrile) and various metal ions (for example of zinc, nickel, iron, silver, and gold). Often, organic solvents or nitriles and/or metal ions coexist with cyanide in industrial waste streams from, for example, synthetic fiber production, electroplating, mining operations, and processing of cassava or bitter almonds.

The cyanide converting enzymes of this invention have been applied successfully (in the laboratory) on several cyanide containing waste waters of highly different chemical compositions.

This invention is further illustrated by the following examples. The cyanide converting enzyme tested was obtained by cultivation of the strain deposited under DSM No. 4009. In Examples 1 through 19, different tests are described. These examples refer to tests and limits stated in some of the following claims. A preferred enzyme mode of this invention is one which fulfills many or all of the tests described in examples.

Enzyme activities in the following examples are expressed in International Units (hereinafter abbreviated IU). One IU of enzyme corresponds to the amount of enzyme which catalyses the conversion of 1 umole of cyanide per minute in 60 mM NaCN at a pH value of 7.0, and a temperature of 30° C.

| CHARACTERIZATION OF ENZYME PREPARATION | | |
|---|---|---|
| Optimum pH: 7.8. | | |
| Stable and active pH range: 6-9. | | |
| Optimum temperature: 40° C. | | |
| Active temperature range (above 20%): 15° C.-50° C. | | |
| Taxonomy of strains DSM 4009 and 4010 | | |
| Properties of the strain | DSM 4009 | DSM 4010 |
| Shape of cells | rods | |
| width μm | 0.5–0.7 | 0.5–0.7 |
| length μm | 0.8–2.5 | 0.8–2.5 |
| Motility | + | + |
| Flagellation | peritrichous | peritrichous |
| Gram reaction | − | − |
| Lysis by 3% KOH | + | + |
| Aminopetidase (Cerny) | + | + |
| Spores | − | − |
| Oxidase | + | + |
| Catalase | + | + |
| Growth | | |
| anaerobic | − | − |
| 37/41° C. | +/− | +/− |
| pH 5.6 | + | + |
| Mac-Conkey-Agar | + | + |
| SS-Agar | + | + |
| Cetrimid-Agar | + | + |
| autotrophic with hydrogen | − | − |
| Pigments | | |
| non diffusible | − | − |
| diffusible | − | − |
| fluorescent | − | − |
| pyocyanine | − | − |
| Acid from (OF-Test) | | |
| glucose aerobic | − | − |
| glucose anaerobic | − | − |
| Gas from glucose | − | − |
| Acid from (ASS) | | |
| glucose | − | − |
| fructose | − | − |
| xylose | − | − |
| ONPG | − | − |
| ADH | − | − |
| LDC | − | − |
| VP | − | − |
| Indol | − | − |
| NO$_2$ from NO$_3$ | + | + |
| Denitrification | + | + |
| Phenylalanine deaminase | − | − |
| Levan from sucrose | − | − |
| Lecithinase | − | − |
| Urease | − | − |
| Hydrolysis of | | |
| starch | − | − |
| gelatin | − | − |
| casein | − | − |
| DNA | − | − |
| Tween 80 | − | − |
| esculin | − | − |
| Tyrosine degradation | − | (nd) |
| Growth factor requirements | − | − |
| Utilization of | | |
| acetate | + | − |
| adipate | + | − |
| caprate | − | − |
| citrate | + | − |
| glycolate | − | (nd) |
| levulinate | − | − |
| malate | + | − |
| malonate | − | (nd) |
| phenylacetate | + | + |
| L-arabinose | − | − |
| fructose | − | − |
| glucose | − | − |
| mannose | − | − |
| maltose | − | − |
| xylose | − | − |
| mannitol | − | − |

CHARACTERIZATION OF ENZYME PREPARATION
Optimum pH: 7.8.
Stable and active pH range: 6–9.
Optimum temperature: 40° C.
Active temperature range (above 20%): 15° C.–50° C.
Taxonomy of strains DSM 4009 and 4010

| Properties of the strain | DSM 4009 | DSM 4010 |
|---|---|---|
| gluconate | − | + |
| 2-ketogluconate | − | (nd) |
| N-acetylglucosamine | − | − |
| L-serine | + | (nd) |

Result:
= *Alcaligenes denitrificans* subsp. *denitrificans*
(nd) = not determined

EXAMPLE 1

Test For Efficacy of Cyanide Detoxification 2.5 IU of the cyanide converting enzyme is added to 5 ml of 0.1 M phosphate buffer (pH value: 7) which is 0.1 M with respect to NaCN. This mixture is incubated with gentle mixing at 37° C. After 60 minutes of incubation, the concentration of residual inorganic cyanide in the reaction mixture is analyzed (employing the Merck Aquaquant ® 14429 test-kit).

Using cyanide converting enzyme obtained from DSM No. 4009, the residual concentration of inorganic cyanide was less than 0.03 ppm. The residual concentrations of inorganic cyanide determined by the aforesaid Aquaquant test-kit was checked at regular intervals using the pyridine-barbituric acid method (cf. American Standard Methods, 15th edition, 1980, 412 D, 320–322) to verify that the inorganic cyanide was indeed reduced below a concentration of 0.03 ppm.

Inorganic cyanide was not hydrolyzed in control experiments without enzyme nor in experiments using boiled enzyme thus proving that the conversion of inorganic cyanide was entirely enzymatic.

EXAMPLE 2

Test For Efficacy of Cyanide Detoxification

Ten ml of the buffer of Example 1 containing 200 mM (5,200 ppm) of NaCN (pH value: 7.5) is treated with 25 IU of the cyanide converting enzyme at 30° C. under gentle mixing. After 2 hours of incubation, the concentration of inorganic cyanide in the reaction mixture is measured.

Using cyanide converting enzyme obtained from DSM No. 4009, the residual concentration of inorganic cyanide was below 0.03 ppm. The ammonia concentration was about 200 mM. Ammonia was assayed according to the method of Chaney and Marbach (Clin.Chem. 8 (1962), 130–132).

EXAMPLE 3

Test for Cyanide Tolerance

A 600 mM solution of NaCN in the buffer of Example 1 (pH value monitored to be between 7.0 and 7.6) is treated with the cyanide converting enzyme (6 IU per ml of solution) at 30° C. under gentle mixing. After 5 hours of incubation, the concentration of inorganic cyanide in the reaction mixture is measured.

Using cyanide converting enzyme obtained from DSM No. 4009, the residual cyanide concentration was below 0.03 ppm. The ammonia concentration was about 600 mM.

EXAMPLE 4

Test for Cyanide Tolerance

A 1,000 mM (approx. 49,000 ppm) solution of NaCN in the buffer of Example 1 (pH value monitored between 7.0 and 7.5) is treated with cyanide converting enzyme (6.0 IU per ml of reaction mixture as measured at 30° C.) and incubated at 22° C. under gentle mixing. After 48 hours of incubation the concentration of inorganic cyanide in the reaction mixture is measured.

Using cyanide converting enzyme obtained from DSM No. 4009 the residual cyanide concentration was below 0.03 ppm. The ammonia concentration was about 1,000 mM.

In a control experiment (i.e. without the addition of enzyme) less than 5% of the initial cyanide disappeared due to air stripping.

EXAMPLE 5

Test for Heat Stability

The test described in Example 3 is repeated except for the temperature being 45° C. After 4 hours of incubation, the concentration of inorganic cyanide in the reaction mixture is measured.

Using cyanide converting enzyme obtained from DSM 4009, the residual concentration of inorganic cyanide was less than 0.03 ppm.

EXAMPLE 6

Test for Heat Stability

The test described in Example 2 is repeated except for the temperature being 45° C. After 2 hours of incubation, the concentration of inorganic cyanide of the reaction mixture is measured.

Using cyanide converting enzyme obtained from DSM 4009, the residual concentration of inorganic cyanide was less than 0.03 ppm.

EXAMPLE 7

Test for Stability Against Acetone (5%)

The buffer of Example 1 containing 5% of acetone (v/v) is made 100 mM with respect to NaCN. This solution (total volume 10 ml, pH value adjusted with phosphoric acid to 7.5) is treated with 13 IU of the cyanide converting enzyme and incubated with gentle mixing at 22° C. After 3 hours of incubation, the concentration of inorganic cyanide in the reaction mixture is measured.

Using cyanide converting enzyme obtained from DSM No. 4009, the residual concentration of inorganic cyanide was below 0.03 ppm.

EXAMPLE 8

Test for Stability Against Acetone (10%)

The test described in Example 7 is repeated with the exception that the aqueous solution contains 10% (v/v) acetone. After 5 hours of incubation the concentration of inorganic cyanide in the reaction mixture is measured.

Using cyanide converting enzyme obtained from DSM 4009, the residual concentration of inorganic cyanide was below 0.03 ppm.

EXAMPLE 9

Test for Stability Against Methacrylonitrile (100 mM)

Thirteen units of the cyanide converting enzyme is added to 10 ml of a 0.1 M phosphate buffer (0.1 M NaCN, 0.1 M methacrylonitrile, pH value 7.5). After 2.3 hours of incubation at about 22° C., the concentration of inorganic cyanide is measured.

Using cyanide converting enzyme obtained from DSM No. 4009, the residual concentration of inorganic cyanide was below 0.03 ppm. Methacrylonitrile was not degraded in the reaction mixture as determined by HPLC analysis using a reverse phase $C_{18}$-column.

EXAMPLE 10

Test for Stability Against Methacrylonitrile (200 mM)

The test described in Example 9 is repeated with the exception that the solution contains 200 mM of methacrylonitrile and the concentration of inorganic cyanide is measured after an incubation of 5.5 hours.

Using cyanide converting enzyme obtained from DSM 4009, the residual concentration of inorganic cyanide in the reaction mixture was below 0.03 ppm. The concentration of methacrylonitrile remained constant throughout the experiment.

EXAMPLE 11

Test for Stability Against Acrylonitrile (100 mM)

25 IU of the cyanide converting enzyme is added to 10 ml of a 0.1 M phosphate buffer (0.12 M NaCN, 0.1 M acrylonitrile, pH value 7.5). After 2 hours of incubation at 25° C., the concentration of inorganic cyanide is measured.

Using cyanide converting enzyme obtained from DSM NO. 4009, the residual concentration of inorganic cyanide was below 0.03 ppm. Acrylonitrile was not degraded as determined by HPLC analysis using a reverse phase $C_{18}$-column.

EXAMPLE 12

Test for Stability Against Acrylonitrile (200 mM)

The test described in Example 11 is repeated with the exception that the aqueous solution contains 1.2 IU of enzyme per ml and 200 mM acrylonitrile.

Using cyanide converting enzyme obtained from DSM 4009, 98.4% of the initial inorganic cyanide was degraded after 2.5 hours. After 6 hours, the residual concentration of inorganic cyanide was below 0.03 ppm.

EXAMPLE 13

Test for Stability Against Acrylonitrile and Methacrylonitrile

The present cyanidase is added to a 0.1 M phosphate buffer (0.05 M NaCN, 0.05 methacrylonitrile, 0.05 M acrylonitrile, pH 7.5) to a concentration of 0.8 IU/ml reaction mixture. After 4 hours of incubation at about 22° C. the concentration of cyanide is measured.

Using cyanide converting enzyme obtained from DSM 4009, the residual concentration of inorganic cyanide was below 0.03 ppm. Acrylonitrile and methacrylonitrile was not degraded in the reaction mixture.

EXAMPLE 14

Test for Stability Against Methanol

The cyanide converting enzyme of DSM 4009 was tested for its activity and stability in the presence of different concentrations of methanol (hereinafter abbreviated MeOH). The results obtained are shown in Table IA and IB.

TABLE IA

| % MeOH (v/v) | Initial Activity* (%) |
| --- | --- |
| 0 = control | 100 |
| 10 | 98–100 |
| 20 | 60–66 |
| 30 | 11–15 |

*The initial activity was measured at 22° C., pH 7.5 and a substrate concentration of 60 mM NaCN in 0.1 M phosphate buffer. The reaction mixture (10 ml) containing 5 IU of cyanide converting enzyme was placed in glass test tubes with teflon lined screw caps and mounted on a rotator. The enzyme used was an immobilized preparation obtained by cross-linking cells of DSM 4009 with glutaraldehyde using standard immobilization procedures.

TABLE IB**

| % Residual Activity after 6 days | % MeOH (v/v) | % Residual Activity after 5 days |
| --- | --- | --- |
| 90 | 0 | 85 |
| 66 | 10 | |
| | 20 | 23 |

**The reaction mixtures of Table IA were stored (tightly closed) for 5 and 6 days, respectively, at 22° C. in the laboratory. The enzyme granules were recovered by centrifugation, washed once with phosphate buffer and tested for activity as described above.

EXAMPLE 15

Detoxification of Cyanide in Waste Water from Zinc Plating Bath

Rinse water from an electroplaters alkaline zinc bath container free cyanide and zinc is treated with a cyanidase according to the invention.

Using the enzyme of DSM 4009 in an amount of 0.6 IU per ml waste water containing 62 ppm free cyanide and 50 ppm zinc the concentration of free cyanide was reduced to less than 1 ppm after 1.5 hours of reaction at 22° C. The pH of the reaction mixture was monitored to be 7.5±0.5 throughout the experiment.

EXAMPLE 16

Detoxification of cyanide From Zinc Plating Bath

The waste water of Example 15 was diluted threefold with tap water, whereby it was found to contain now 20 ppm free cyanide and 17 ppm zinc.

Using the cyanidase of DSM 4009 at a concentration of 0.6 IU per ml reaction mixture the concentration of free cyanide was reduced to less than 1 ppm in 30 minutes at 22° C. During the reaction pH was monitored to be 7.5±0.5 through the experiment.

TABLE II

| Reduction in Free Cyanide in Solutions of 2 mM Metal Ion and 60 mM NaCN, pH 7.8 | | |
| --- | --- | --- |
| Metal | Cyanidase IU/ml Reaction Mixture | CN- at 72 h ppm |
| $Zn^{2+}$ | 0.41 | <0.03 |
| $Ni^{2+}$ | 0.43 | <0.3 |
| $Fe^{2+}$ | 0.44 | <0.03 |
| $Fe^{3+}$ | 0.40 | <0.03 |
| Control | 0.33 | >0.03 |

TABLE III

Reduction in Free Cyanide in Solutions of 4 mM Metal Ion and 120 mM NaCN, pH 7.8

| Metal | Cyanidase IU/ml Reaction Mixture | CN- at 22 h ppm |
|---|---|---|
| $Zn^{2+}$ | 0.67 | <0.03 |
| $Ni^{2+}$ | 0.67 | <0.03 |
| $Fe^{2+}$ | 0.64 | <0.03 |
| $Fe^{3+}$ | 0.58 | <0.03 |
| Control | 0.70 | <0.03 |

EXAMPLE 17

Detoxification of Cyanide in Waste Water from Marcipan Production

The cyanidase from DSM 4009 was used for the detoxification of waste water originating from the debittering of apricot kernels in the production of marcipan. The waste water contained 95 ppm free cyanide. By reacting this waste water at 22° C. for 4 hours with 0.6 IU cyanidase per ml reaction mixture while keeping pH of the reaction mixture at 7.5 by addition of dilute sodium hydroxide, the cyanide content was reduced to less than 1 ppm free cyanide.

EXAMPLE 18

Detoxification of Cyanide in the Presence of Metal Ions

The cyanidase from DSM 4009 was used for the detoxification of cyanide in solutions of metal ions ($Zn^{2+}$, $Ni^{2+}$, $Fe^{2+}$, $Fe^{3+}$) in the buffer of Example 1.

By reacting solutions of each of the above metal ions containing free cyanide with the cyanidase of the invention the content of free cyanide was reduced as shown in Table II and III below.

From the tables it is seen that the present cyanidase enzyme is efficient in reducing substantial amounts of cyanide to very low levels in the presence of various metal ions.

EXAMPLE 19

Test for Storage Stability

Washed cells obtained as described in Example 21 are stored in clear glass bottles (0.1 M phosphate buffer, pH value 7) in the laboratory under the prevailing light conditions and temperature 22° C.±2° C.

After 30 days of storage more than about 95% of the initial enzyme activity remained within the cells using an enzyme obtained from DSM 4009.

EXAMPLE 20

Cultivations of Strains (DSM 4009)

The strains were maintained on slants of nutrient broth containing 2% agar. Nutrient broth was purchased from Difco Laboratories (Detroit, Michigan, USA). Liquid culturing was carried out in 500 ml shake flasks containing 100 ml of nutrient broth medium supplemented with 1% glycerol. Incubation was at 30° C. for approximately 24 hours with good aeration. Induction of cyanide converting enzymes was done after 8-10 hours of growth by adding NaCN (1 mM) to the growing culture. Bacterial cells were recovered by centrifugation, washed and stored at 4° C. or freeze-dried. If desired, the cyanide converting enzymes may be isolated and purified in manners known per se.

Constitutive strains are cultivated as above, the only difference being that no induction of the cyanide converting enzyme production is necessary.

EXAMPLE 21

Production of Enzyme Preparation (Whole Cell) From DSM 4009

Cells cultivated as described in Example 20 were harvested by centrifugation and washed one to three times with 0.1 M phosphate buffer (pH 7).

Washed cell suspensions of different cell densities (and thus different activity) were stored at 4° C. in 0.1 M phosphate buffer. Alternatively washed cell suspensions were freeze-dried or stored at −25° C.

Washed cell suspensions were used in the experiments described in Examples 1, 2, 3, 5, 6, 7, 8, 9, 10, 11, 12, 13, 15, 16, 17 and 19.

EXAMPLE 22

Production of an Immobilized Cell Preparation of DSM 4009

The cell bound cyanidase of DSM 4009 were immobilized by cross-linking whole washed cells (obtained as described in Example 21) using standard immobilization techniques using e.g. glutaraldehyde as cross-linking agent.

Cells immobilized by cross-linking with glutaraldehyde were used in the experiments described in Examples 4, 14 and 18.

We claim:

1. Cyanidase, a cyanide converting enzyme of bacterial origin which converts inorganic cyanide to formic acid and ammonia, said enzyme being characterized by enzymatic activity in the presence of sodium cyanide at a concentration above about 0.1M and by an enzymatic capability to reduce inorganic cyanide to below about 1 ppm.

2. A cyanidase according to claim 1 having a pH optimum in the range of pH 6-9.

3. A cyanidase according to claim 1 further characterized by capability of converting cyanide in the presence of organic solvents.

4. A cyanidase according to claim 1 further characterized by capacity of converting cyanide in the presence of metal ions.

5. A cyanidase according to claim 1 further characterized by capability of converting cyanide in the presence of ions of a metal selected from the group consisting of zinc, nickel, iron, gold, and silver.

6. A cyanidase according to claim 1 further characterized by capability of converting inorganic cyanide to a residual cyanide content below about 0.1 ppm and by enzymatic activity in the presence of sodium cyanide at a concentration above bout 0.5M.

7. Cyanidase, a cyanide converting enzyme of bacterial origin according to claim 1 further characterized by capability to hydrolyze inorganic cyanide in the presence of methanol, ethanol, acrylonitrile, methacrylonitrile or ions of a metal selected from the group consisting of zinc, nickel, iron, gold, and silver.

8. A cyanide converting enzyme elaborated by the microorganism of the Accession No. DSM 4009.

9. A cyanide converting enzyme elaborated by the microorganism of the Accession No. DSM 4010.

10. A process for the production of a cyanidase by cultivating a cyanidase producing strain of *Alcaligenes denitrificans* subspecies denitrificans in the presence of a source of assimilable nitrogen, carbon and oxygen, plus essential nutrients, and subsequently recovering the cyanidase, said cyanidase being a cyanide converting enzyme which converts inorganic cyanide to formic acid and ammonia, said enzyme being characterized by enzymatic activity in the presence of sodium cyanide at a concentration above about 0.1M and by an enzymatic capability to reduce inorganic cyanide to below about 1 ppm.

11. A process according to claim 10, wherein said strain has the Accession No. DSM 4009.

12. A process according to claim 10, wherein said strain has the Accession No. DSM 4010.

13. A process according to claim 10 wherein said strain is a constitutive mutant strain from DSM 4009.

14. A cyanidase according to claim 1 further comprising an enzymatically active cell mass preparation.

15. A cyanidase preparation according to claim 14 in cross-linked immobilized form.

16. A method for detoxification of cyanide containing streams which comprises contacting such a stream with a cyanidase which converts inorganic cyanide to formic acid and ammonia, said enzyme being characterized by enzymatic activity in the presence of sodium cyanide at a concentration above about 0.1M and by an enzymatic capability to reduce inorganic cyanide to below about 1 ppm.

17. A method according to claim 16 wherein said cyanide containing stream is at a pH in the range of pH 4-11 and at a temperature in the range of 20°-50° C.

18. A method according to claim 16 wherein said cyanide containing stream is at a pH in the range of pH 6-9.

19. A method according to claim 16 further comprising enzymatically reducing the cyanide content in said cyanide containing stream to below about 0.1 ppm.

20. A method according to claim 16 wherein said cyanide containing stream contains one or more of acetone, methanol, methacrylonitrile, acrylonitrile, and ions of a metal selected from the group of zinc, nickel, iron, gold and silver.

* * * * *